United States Patent [19]

Behpour et al.

[11] 4,182,770

[45] Jan. 8, 1980

[54] ALCOHOL DETERRENT

[75] Inventors: Ahmad Behpour, Berlin; Detlev Kayser, Darmstadt; Gerhard Martin, Wiesbaden, all of Fed. Rep. of Germany

[73] Assignee: Merck Patent Gesellschaft mit beschraenkter Haftung, Darmstadt, Fed. Rep. of Germany

[21] Appl. No.: 3,695

[22] Filed: Jan. 16, 1979

Related U.S. Application Data

[63] Continuation of Ser. No. 840,203, Oct. 7, 1977, abandoned.

[30] Foreign Application Priority Data

Oct. 9, 1976 [DE] Fed. Rep. of Germany ....... 2645709

[51] Int. Cl.$^2$ .......................................... A61K 31/415
[52] U.S. Cl. ................................................ 424/273 R
[58] Field of Search ................................... 424/273 R

[56] References Cited

FOREIGN PATENT DOCUMENTS 1620043 3/1970 Fed. Rep. of Germany .
1133408 11/1968 United Kingdom .

OTHER PUBLICATIONS

Hahn, J., Inaugural Dissertation; Giessen 1974.

*Primary Examiner*—Donald B. Moyer
*Attorney, Agent, or Firm*—Millen & White

[57] ABSTRACT

1-(4-nitrophenyl)-2-methyl-4-nitroimidazole has been found to be highly useful as an alcohol deterrent.

12 Claims, No Drawings

ALCOHOL DETERRENT

This is a continuation, or application Ser. No. 840,203 filed Oct. 7, 1977.

BACKGROUND OF THE INVENTION

This invention concerns an agent for achievement of an aversion to alcohol in humans.

Orally administered agents which act as a deterrent to the use of alcohol are known. Presently, the best-known such active material is disulfiram. However, this material displays several undesirable side effects. For example, its use is contraindicated by, inter alia, diabetes. Furthermore, effective dosaging of disulfiram requires daily administration. Such a regimen is troublesome and difficult to maintain, especially in the case of ambulant treatment.

SUMMARY OF THE INVENTION

Thus, it is an object of this invention to provide an alcohol deterrent which minimizes the disadvantages of the known deterrents.

This and other objects of this invention have been attained by the discovery that administration, e.g., orally of 1-(4-nitrophenyl)-2-methyl-4-nitroimidazole (I) causes an aversion to alcohol in humans.

Consequently, in a composition aspect, this invention involves a new alcohol deterrent composition containing an effective dose of I.

Furthermore, in a method of use aspect, this invention relates to a method for developing an aversion to alcohol in humans by administering an effective dose of compound I. It also relates to a method for disaccumstoming a human from the habit of using alcohol which comprises administering an effective dose of compound I.

DETAILED DISCUSSION

The substance (I) is known (cf. published German Patent Specification P 16 20 043 or equivalent British Pat. No. 1,133,408), as is its effectiveness against disease-causing trichomonads, amoeba and trypanosomes. However, none of the known uses would indicate to a skilled worker that the substance I can be used as an alcohol deterrent.

The composition of this invention is suitable for administration to humans in all cases in which the intake of alcohol is to be lessened. Thus, it is highly appropriate for administration to healthy humans, e.g., those not suffering from trichomonad, amoebic or trypanosomic diseases. For alcoholics, it can be used as a disaccustoming agent, whereby it permits the achievement of a temporary alcohol withdrawal, which of course, is regarded as a valuable result.

The compositions can be prepared in conventional fashion by admixing the substance I with at least one pharmaceutically acceptable carrier or adjuvant material and, optionally, with one or more additional active materials, in a suitable dosage form. The compositions thus obtained can be employed as agents for the achievement of an aversion to alcohol in humans or as agents for disaccustoming a human from alcohol.

Suitable carrier substance include organic or inorganic materials which are suitable for enteral, e.g., oral or for parenteral administration and do not react with the substance I, for example, water, vegetable oils, benzyl alcohols, gelatine, carbohydrates, such as lactose or starch, magnesium stearate, talc etc. For oral administration, tablets, dragees or capsules are especially suitable; but syrups, juices, drops etc. can also be employed. For parenteral administration, solutions, preferably oily solutions are suitable, but suspensions or implants etc. can also be used. The compositions of this invention can be sterilized and/or contain adjuvant materials, such as lubricating, preserving, stabilizing and/or wetting agents, emulsifiers, salts for influencing the osmotic pressure, buffer substances, coloring, flavoring and/or aroma generating materials and the like.

In a preferred form, the compositions of this invention can be formulated with one or more active ingredients such as aspirin, vitamins and other food supplements, etc.

The latter additives are particularly appropriate since alcoholics often suffer from nutritional deficiencies. Suitable active ingredients include the vitamin B group, vitamin C, vitamins A, $D_2$, $D_3$ and E, nicotinamide, pantothenic acid and its salts, such as the Ca salt, rutin, mineral salts, such as the chlorides, sulfates or phosphates of Ca, Co, Cu, Fe, Mg, Mn and Zn.

The compositions of this invention preferably contain the active material I in oral or parenteral dosages between about 200 and 2000, preferably between 600 and 1000 and especially about 800 mg. per dosage unit along with from 10 to 5000 mg. of carrier and from 0 to 1000, preferably from 30 to 200 mg. of additional active ingredient. The daily dosage preferably lies between about 4 and 40 mg./kg. of body weight, if the preparation is given daily.

However, as a result of the high half-life time of the active material I, which amounts to more than 40 hours, it is also advantageously possible to administer the compositions less frequently, e.g., every third day or even only once a week. Consequently, it is possible, for the first time, to have a dosage regimen with long intervals between administrations. In such a regimen the dosages are set so that the dosage available during the final 24 hours period of a given interval, accounting for the half life of I, is equivalent to the daily dosage described above.

Because of the necessarily short intervals required for the administration of the conventional active materials, control of administration was not possible. By means of the new agent, however, convenient control of administration is now possible.

In a particularly preferred mode of administration, tablets or dragees containing about 800 mg. of I are used. As an example of its use, after at least 12 hours of alcohol abstention, a half tablet (400 mg.) can be given in the morning before eating, and another half on the next day.

The appropriate dose for any particular use depends, in each case, upon the usual factors, for example, age, body weight, general state of health, sex, diet, time and route of administration, presences of alcoholism etc. Appropriate dosages for an individual can be determined by conventional considerations but the dosages described above are generally effective.

After the administration of I, a pronounced revulsion against alcohol is produced. It can even appear upon merely smelling the atmosphere of a barroom. The side effects which occasionally appear are, generally minor. They consist mainly of tachycardia, flush-like skin reddenings, sickly feelings, headache and hangover. However, in comparison with the known severe results of a marked abuse of alcohol, these side effects are negligible.

It has been demonstrated biochemically that the alcohol imcompatibility brought about by I is due exclusively to an increase in the acetaldehyde content of the blood after the consumption of alcohol. In contrast, important enzyme systems are inhibited by use of disulfiram. No such inhibition occurs with use of compound I which consequently can be used to treat alcoholics who also suffer from diabetes.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

Case Histories

22 Men and 5 women were treated with the new agent I. The youngest patient was 22 and the oldest 68. The average age was 44 years. After the first administration (400 mg., twice), as described above, the dosage consisted of a single oral administration of 800 mg. per week. The highest total dosage amounted to 67 g. of I. With this, the patient could be protected against the influence of alcohol for 84 weeks.

EXAMPLE 1

Total dosage of I: 67 g.

Subject: a 36 year old champagne cellerman, under medical treatment since 1959.

Anamnesis (A):

1959: Ascites with tumor cells, laparotomy without tumor findings. 1962: Pleuritis with tumor cells, Cyclophosphamide treatment, florid liver cell damage, diabetes mellitus; disability pension. Since 1964 part time work (6 hours daily).

Alcohol anamnesis (AA):

1966: Hospitalization: delirious symptoms of a chronic alcohol intoxication. 1968 hospitalization: praecoma hepaticum, alcohol delirium hemorrhage of oesophageal varices. 1970 hospitalization: alcohol delirium.

In May 1972, the patient again came to the hospital delirious. He kept free of alcohol for 24 hours. Treatment then commenced with 400 mg. of I. Good compatibility. Further administration of 400 mg. on the following day and thereafter 800 mg., once a week. From then on, the patient behaved normally and worked regularly. At the end of March 1973, by way of experiment, there was a pause in the treatment. May 1974: severe collapse. His wife admitted that he drank beer in comparatively large quantities. The treatment began again with the same good success up to January 1975. After conversion to placebo treatment, the patient remained normal.

EXAMPLE 2

Total dosage of I: 57 g.

Subject: a 38 year old storekeeper under medical treatment since 1962.

A:

Numerous injuries in accidents and fights.

AA:

In October 1973, received alcohol withdrawal treatment in private clinic. After release, still alcoholneurotic difficulties. Consequently, from November 1973 to February 1974, treatment with I. One month after discontinuation of the treatment, throbbing headache caused by alcohol. Since April 1974, with relatively regular taking of tablets, normal, regular work.

EXAMPLE 3

Total dosage of I: 37 g.

Subject: unemployed under medical treatment since 1969.

A:

Chondrodystrophic female dwarf. Since 1972, increasing blood sinking reaction and increasing liver values in spite of energetic liver treatment (infusions).

AA:

Admitted excessive wine consumption. First treatment from August to November 1972. Towards the end of 1973, again increasing alcohol consumption. Therefore, renewed treatment from November 1973 to January 1975. Since then no alcohol.

EXAMPLE 4

Total dosage of I: 25 g.

Subject: a 54 year old Greek immigrant worker under medical treatment since 1965.

A:

1965: Gastric stenosis in the bulbus region; 1970: diabetes mellitus, appendectomy.

AA:

In March 1974, his wife stated that every day he returned from work drunk. After initiation of the treatment, his wife expressed thanks for the successful breaking of the habit. Since the end of the treatment, according to statements of the wife, he only had an occassional 1–2 glasses of wine, somewhat more when he is on holiday in Greece.

EXAMPLE 5

Total dosage of I: 17 g.

Subject: a 44 year old employee sent by colleagues for a withdrawal treatment

In the investigation, a latent diabetes mellitus and a latent sideropenia were found. Withdrawal treatment: from September 1974 to February 1975, terminated by mutual agreement. Since then, alcohol-free.

In assessment of success, 5 cases are to be discounted from the total of 27 I treatments. In one case, testing was made only for alcoholism; in another one, the patient was only drunk once; and in three cases, the patients did not reappear after taking the tablets once. Thus, 22 cases remain which can be considered as I treatments. In 12 of these cases, the withdrawal treatment was successful; in three cases questionable; and 7 cases without success. The success of the treatment is clearly correlated with the period of the withdrawal treatment. After taking 11 g. of I and more (corresponding to an active level period of over 14 weeks), 8 successful cases were counted and two had questionable success. Below 6 g. of I (corresponding to an active level of not more than 8 weeks), there were seven failures; one questionable case and only 2 successful withdrawals.

In addition to the treatment with I, critical examinations for possible damages were undertaken. Determinations of lymphocytes, bilirubin in the blood, GT, GOT, GPT, total protein, $\beta$-globulins, $\gamma$-globulins, cholesterol and RR systolic, produced no indications of harmful side effects. To the contrary, the liver function tests (bilirubin in the blood, $\gamma$-GT and $\gamma$-globulins) indicated clear normalizations. However, this observation probably only applies indirectly and exclusively to alcohol-toxic liver damages because toxic alcohol which was no longer inhibited, no longer acted upon the liver.

Galenical Examples

The following examples concern pharmaceutical compositions which contain the substance I.

EXAMPLE A: Tablets

A mixture of 8 kg. of I, 900 g. of lactose, 800 g. of maize starch, 720 g. of potato starch, 860 g. of cellulose powder, 432 g. of highly dispersed silicic acid, 144 g. of sodium carboxymethylcellulose and 144 g. of magnesium stearate was pressed into tablets using conventional procedures such that each tablet contained 800 mg. of I.

EXAMPLE B: Dragees

In analogous manner to Example A, tablets were pressed and subsequently conventionally coated with a coating of saccharose, potato starch, talc, tragacanth and coloring material.

EXAMPLE C: Capsules

A mixture of 2 kg. of I, 4.5 kg. of lactose and 40 g. of magnesium stearate was conventionally filled into hard gelatine capsules so that each capsule contained 200 mg. of I.

EXAMPLE D: Capsules

A mixture of 4 kg. of I, 1.247 kg. of lactose and 53 g. of magnesium stearate was conventionally filled into hard gelatine capsules so that each capsule contained 400 mg. of I.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of deterring a human from consuming alcohol which comprises administering to a human whose intake of alcohol is to be lessened, successive doses of 1-(4-nitrophenyl)-2-methyl-4-nitroimidazole at least until the consumption of alcohol by the human is substantially reduced.

2. The method of claim 1 wherein the administering is oral or parenteral.

3. The method of claim 2 wherein the administering is by injection.

4. The method of claim 1 wherein the human is not suffering from trichomonad, amoebic or trypanosomic diseases.

5. The method of claim 4 wherein the human has diabetes.

6. The method of claim 1 wherein the human also has diabetes.

7. The method of claim 1 wherein the human host is not suffering from alcoholism.

8. The method of claim 1 wherein the human host is suffering from alcoholism.

9. The method of claim 1 wherein the administration of the nitroimidazole is less frequently than daily.

10. The method of claim 9 wherein the total dosage administered to the human is more than 11 grams.

11. The method of claim 9 wherein the administration is not more frequently than every third day.

12. A method of deterring a human from consuming alcohol which comprises administering to a human whose intake of alcohol is desired to be lessened, an amount of 1-(4-nitrophenyl)-2-methyl-4-nitroimidazole effective for deterring the human from the consumption of alcohol.

* * * * *